United States Patent [19]

Daniel et al.

[11] Patent Number: 4,969,471
[45] Date of Patent: Nov. 13, 1990

[54] KNEE LIGAMENT TESTING DEVICE AND METHOD OF USE

[75] Inventors: Dale M. Daniel, La Mesa; K. Richard Watkins, San Diego, both of Calif.

[73] Assignee: MedMetric Corporation, San Diego, Calif.

[21] Appl. No.: 295,108

[22] Filed: Jan. 9, 1989

[51] Int. Cl.[5] .......................................... A61B 5/103
[52] U.S. Cl. ..................................... 128/774; 128/782
[58] Field of Search ................................ 128/782, 775

[56] References Cited

U.S. PATENT DOCUMENTS

| | | | |
|---|---|---|---|
| 4,220,163 | 9/1980 | Afzali | 128/782 |
| 4,501,266 | 2/1985 | McDaniel | 128/774 |
| 4,799,997 | 1/1989 | Riley | 128/774 |
| 4,823,807 | 4/1989 | Russell et al. | 128/774 |
| 4,834,057 | 5/1989 | McLeod, Jr. | 128/782 |

Primary Examiner—Randall L. Green
Assistant Examiner—K. M. Reichle
Attorney, Agent, or Firm—Neil K. Nydegger

[57] ABSTRACT

A device for measuring displacement of the tibia from a stationarily held patella in response to a specific anterior/posterior force applied on the tibia comprises a reference member which establishes a fixed reference line extending from the patella to a region located distally on the tibia. A measurement member has one end hingedly attached to the reference member and its other end slidingly attached to a tibia paddle which rests on the proximal region of the tibia. A rotatable yoke on the tibia paddle has one prong which rests on the lateral flare of the tibia while another prong of the yoke rests on the medial flare of the tibia. In response to a specific anterior/posterior force: the measurement arm is angled with respect to the reference member in proportion to the anterior/posterior displacement of the tibia; the paddle is moved with respect to the measurement member in proportion to the medial/lateral displacement of the tibia; and the yoke is rotated in angulation proportional to the rotation of the tibia about the proximal/distal axis. A sensor is respectively associated with the measurement member, the paddle and the yoke to record the resultant displacements.

16 Claims, 5 Drawing Sheets

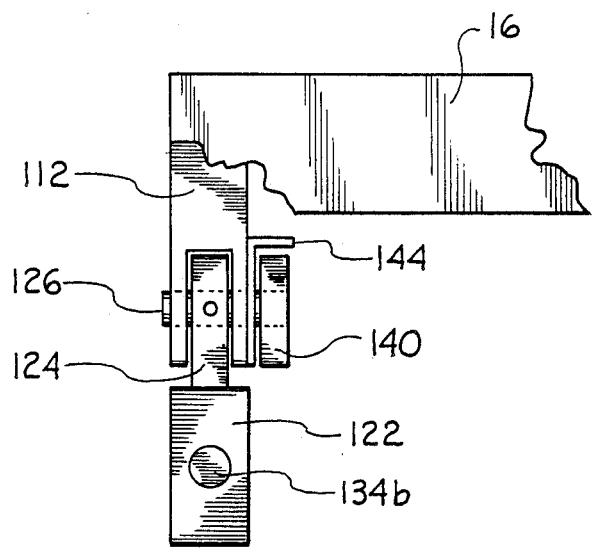
_Fig. 5_
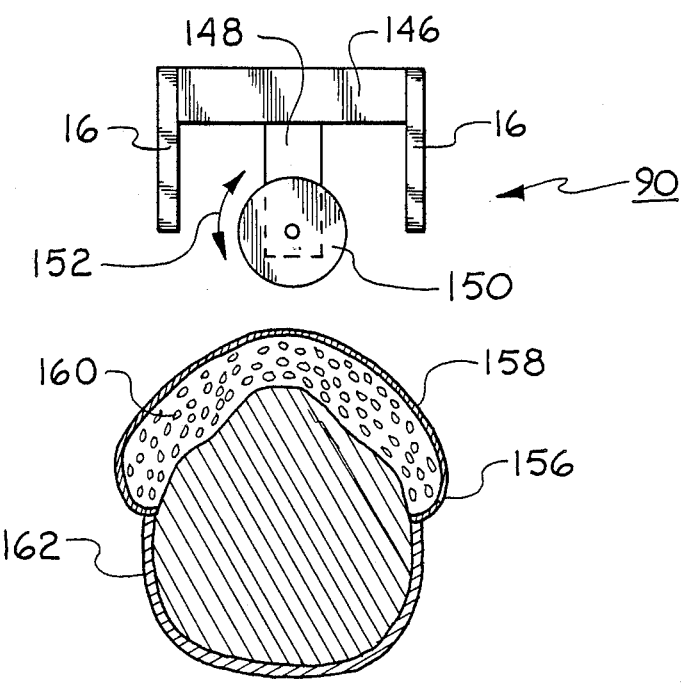
_Fig. 6_

KNEE LIGAMENT TESTING DEVICE AND METHOD OF USE

BACKGROUND OF THE INVENTION

This invention pertains generally to orthopedic measuring devices. More particularly, the present invention pertains to measuring devices which are able to simultaneously measure mutually perpendicular linear displacements and angular displacements about an axis substantially perpendicular to the plane of the linear displacements. The present invention is particularly, but not exclusively, useful for measuring linear and angular displacements of the tibia with respect to the patella for the purpose of testing cruciate ligaments in the knee.

DISCUSSION OF THE PRIOR ART

Traumatic injuries can be very painful and debilitating. In many cases, however, an early diagnosis of the damage and the extent of the damage can significantly help in prescribing proper treatment for alleviating the pain and minimizing the debilitation.

Unlike many of the other types of traumatic injuries which can befall a person, injuries to joints frequently result in impaired or abnormal movement between the connected bone structures. Thus, the ability to determine actual relative movement between the bones which are connected together at the affected joint can be very valuable in making a proper diagnosis. Although the knee is but one example of a joint where diagnoses routinely include an evaluation of joint movement, the knee is a joint which is highly susceptible to injury. This is particularly so when one realizes that knees bear disproportionately the brunt of sports injuries.

As can be easily appreciated, the human knee is a very complex structure. In essence, the knee is a hinge-joint consisting of three rotational and three translational articulations which involve interconnecting tendons, cartilages and ligaments. Fortunately, much information can be obtained concerning damage to the knee and the extent of this damage by merely observing the knee's ability to move the lower leg (i.e. tibia) with respect to the upper leg (i.e. femur). Indeed, acceptable protocols have been established for this purpose. Typically, these protocols require manual movement of the tibia while the femur is held stationary. Manipulation of the leg, however, has certain inherent disadvantages. For one, the individual performing the examination must have very specialized training. Furthermore, the conduct of the examination will vary from individual to individual depending on their application of forces to the leg and their particular feel of the leg's response to the applied force. Additionally, the size of the patient affects the examiner's ability to grasp the patient's leg during performance of the examination and this can influence the results of the examination. For these reasons, and more which need not be recited here, there has been a recognition that an instrumented measurement system would be helpful in standardizing knee movement examination.

Literature pertaining to the KT1000 Knee Ligament Arthrometer manufactured by MEDmetric Corporation and the disclosure in U.S. Pat. No. 4,583,555 by Malcolm et al. for an invention entitled "Knee Ligament Testing System" represent effective attempts to document anterior and posterior displacements of the tibia relative to the femur with instrumented measurements. With devices, such as the KT1000, many of the inherent difficulties encountered by hand manipulation of the leg are obviated. Specifically, with such an instrument, the applied force can be accurately determined and precisely applied regardless of patient size. Further, as with the KT1000, the extent of anterior/posterior displacement of the tibia from the femur can be precisely measured and quantified.

The present invention recognizes that when using accepted protocols, there is more than just anterior/posterior movement between the tibia and the femur. The present invention recognizes that when the femur is held stationary and an anterior/posterior force is applied to the tibia, the tibia will move relative to the femur through at least three distinguishable displacements. Specifically, in response to an anterior/posterior force, the tibia can be expected to translate in the anterior/posterior plane, translate in the medial/lateral plane and rotate about the proximal/distal axis. As appreciated by the present invention, the determination of these particular displacements in response to an applied force of known magnitude under controlled circumstances, can be of significant help in making a proper diagnosis of damage to the knee.

In light of the above, it is an object of the present invention to provide a device which can be repetitively employed to obtain substantially similar conditions for measuring displacements of the tibia relative to the femur. Another object of the present invention is to provide a device which is able to simultaneously measure translation of the tibia in the anterior/posterior plane, translation of the tibia in the medial/lateral plane, and rotation of the tibia about the proximal/distal axis. Still another object of the present invention is to provide a device which standardizes measurements and accurately correlates tibial displacements relative to the femur with the magnitude of the applied force. Yet another object of the present invention is to provide a device which is easy to use and relatively simple to operate. Another object of the present invention is to provide a device which is relatively easy to manufacture and cost effective.

SUMMARY OF THE INVENTION

In accordance with the present invention, a device for measuring displacements of the tibia relative to the femur through the patella held firmly in the trochlear notch comprises a patella reference member which establishes a datum and a tibia reference member which measures movement of the tibia relative to the datum. For easy reference, the patella reference member and the tibia reference member each have a distal and a proximal end which respectively correspond to the distal and proximal ends of the lower leg against which the members are operatively positioned. The patella reference member (i.e. reference member) and the tibia reference member (i.e. measurement member) are each generally elongated structures which are hinged together at their distal ends to establish a fulcrum. Opposite from this fulcrum, the patella reference member has a pad at its proximal end which is adapted to rest against the patella. When this pad is placed against the patella and the fulcrum is positioned at a region on the distal portion of the tibia, the patella reference member establishes a reference line relative to which the tibia reference member can be angled in the anterior/posterior plane.

A tibia paddle includes a mount which is slidingly attached to the proximal end of the tibia reference member in an orientation which permits movement of the mount in the medial/lateral direction relative to the tibia reference member. Also included as part of the tibia paddle is a yoke which is attached to the mount for rotation about an axis that is substantially parallel to the tibia reference member. The yoke is configured to straddle the tibial tubercle and accordingly is formed with two prongs, one of which is adapted to rest on the lateral flare of the tibia and the other of which is adapted to rest on the medial flare of the tibia.

In accordance with the present invention, the tibial displacement measuring device further comprises a plurality of straps which securely holds the device against the lower leg during the displacement testing. Specifically, a distal strap is provided to stationarily hold the fulcrum against a distal region of the tibia and a proximal strap is provided to securely hold the device against the lower leg.

Individual sensor means are respectively attached to the tibia reference member, the mount and the yoke. These attachments correspondingly enable the determination of displacements of the tibia from the patella in the anterior/posterior plane, the medial/lateral plane, and about the proximal/distal axis in response to a predetermined anterior/posterior force applied to the tibia. Specifically, a sensor associated with the tibia reference member is intended to generate a signal which is proportional to the change in angular displacement between the tibia reference member and the patella reference member in response to the specific anterior/posterior force. Stated differently, this sensor measures movement of the tibia between a first position wherein the tibia is resting or unforced and a second position in which the tibia is subjected to the anterior/posterior force. Also, another sensor is associated with the mount to generate a signal proportional to the medial/lateral movement of the mount as the tibia is moved from the first position to the second position. Additionally, still another sensor is associated with the yoke to determine the relative displacement of the lateral flare and the medial flare in their angular orientation to the patella as the tibia is moved between the first and second positions. Further, the present invention contemplates either visual or audio means to indicate when the specific predetermined anterior/posterior force has been achieved.

In accordance with accepted medical diagnosis, the above-described displacements of the tibia relative to the patella can be used to measure knee stability. More specifically, the testing device of the present invention is intended to evaluate the integrity of the ligaments of the knee.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 5 is a side view of the tibial mount and yoke combination shown in FIG. 4 with portions cut away for clarity; and FIG. 6 is a front view of the measurement arm of an alternate embodiment of the device and a cross-sectional view of the associated calf surroundingly attached to the lower leg.

DESCRIPTION OF THE PREFERRED EMBODIMENT

Figure 1:
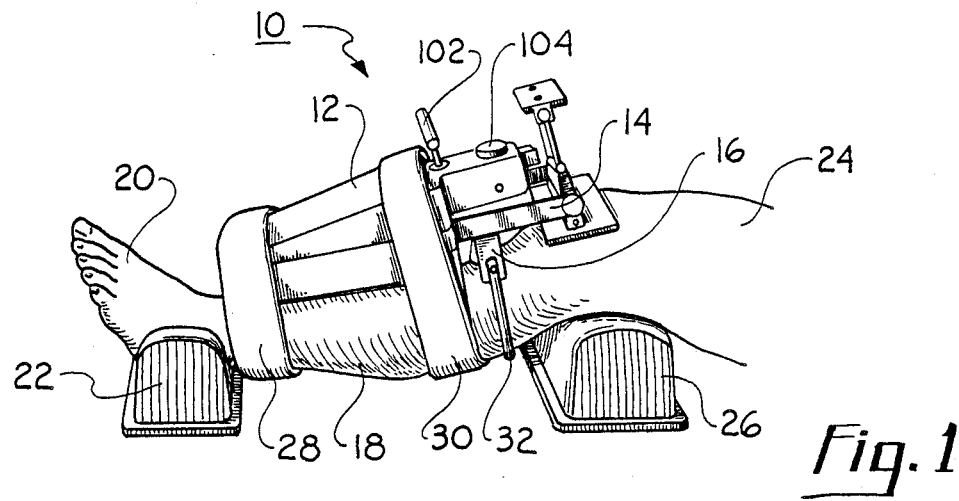
FIG. 1 is a perspective view of the device operatively attached to the lower leg of a patient.

Referring initially to FIG. 1, the device of the present invention is generally designated 10 and shown operatively positioned on a patient. As shown, device 10 comprises a casing 12 which acts as a base that supports and encloses a patella reference arm 14 (sometimes hereinafter referred to as the reference member) and a tibia reference arm 16 (sometimes hereinafter referred to as the measurement member). For purposes of the present invention, the lower leg 18 of a patient is held in a testing position with the patient's foot 20 resting in a foot support 22 and the patient's thigh 24 draped over thigh support 26 to place the knee in twenty-five degrees plus or minus five degrees ($25° \pm 5°$) of flexion. The device 10 is then held against the patient's lower leg 18 by a distal strap 28 and a proximal strap 30. A retainer strap 32 is used to hold the proximal end of tibia reference arm 16 against lower leg 18 for purposes which will be better appreciated after subsequent disclosure.

In order to understand device 10 and its operation, some appreciation of the anatomy of lower leg 18 is helpful. For this purpose, reference is made to FIG. 2 in which the structure of lower leg 18 is shown. More specifically, the bone structure in this part of the body is such that the femur 34 is joined at the knee to the tibia 36 and fibula 38 of lower leg 18. The patella (kneecap) 40 is anteriorly located between femur 34 and tibia 36 substantially as shown. Importantly, on tibia 36 near patella 40 is a boney protuberance known as the tibial tubercle 42 and to each side of tubercle 42 are relatively flat areas which are referred to as the lateral flare 44 and the medial flare 46.

As mentioned above, the connective tissues between femur 34 and tibia 36 are extremely complex. Indeed, a detailed anatomical description of these tissues is not essential to an understanding of the present invention and is beyond the scope of this disclosure. Nevertheless, a general appreciation of the jointed connection which makes up the knee is valuable. In general, the femur 34 and tibia 36 are held together and connected by numerous internal and external ligaments and are structurally cushioned by various cartilages. Many of these restraints are tested during operation of the device 10. For example, the ACL (Anterior Cruciate Ligament), PCL (Posterior Cruciate Ligament), LLPR (Lateral Longitudinal Patellar Retinaculum), MTPR (Medial Transverse Patellar Retinaculum), MLPR (Medial Longitudinal Patellar Retinaculum), MCL (Medial Collateral Ligament), and LCL (Lateral Collateral Ligament), to name a few, are tested by device 10. When viewed as a complex, these and other structures resist displacement forces and may be thought of as tethers. Though no cartilages are shown in FIG. 2A and most of the ligaments are not shown, FIG. 2A does show the general location of the cruciate ligaments (so called because they cross each other somewhat like the lines of the letter X) which are of utmost importance for determining knee laxity. As shown in FIG. 2A, the cruciate ligaments comprise the anterior cruciate ligament 48 and the posterior cruciate ligament 50. How well these ligaments accomplish their proper function can be determined, at least to some extent, by observing the extent to which tibia 36 can be moved relative to femur 34 when the femur 34 is held immobile and a force of predetermined magnitude is applied to the tibia 36. For anatomical reasons, actual displacements of tibia 36 are measured in reference to patella 40 rather than femur 34. It happens, however, that since the patella is held immobile in the femoral trochlea during testing, only negligible movement between patella 40 and femur 34 is possible (i.e. patella 40 is effectively part of femur 34). Therefore, this substitution introduces no significant errors.

Figure 2:
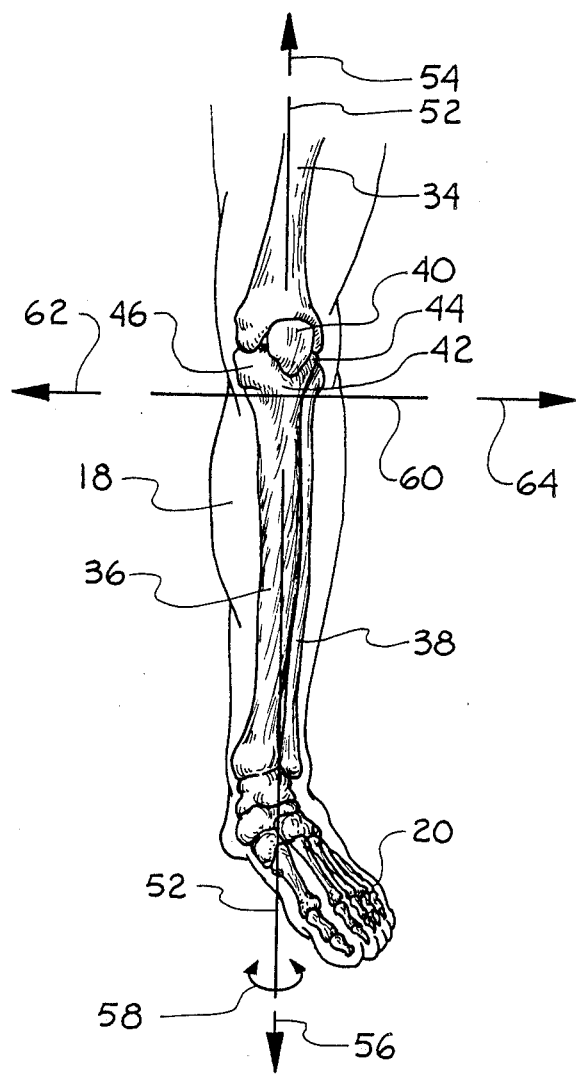
FIG. 2 is a front view of the lower left leg of a patient.
Figure 2A:
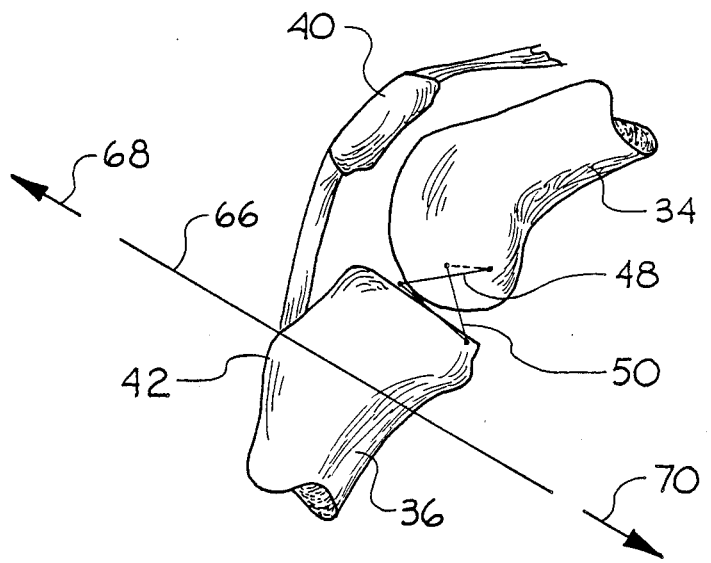
FIG. 2A is a schematic side view of a knee joint.

For purposes of describing the spatial relation and relative displacements between femur 34 and tibia 36, cross-reference is required between FIG. 2 and FIG. 2A. With this cross-reference, the appropriate coordinate system and its orthogonal axes in their relation to lower leg 18 can be established. Specifically, in FIG. 2 it will be seen that proximal/distal axis 52 is substantially aligned along tibia 36. Accordingly, displacements in the proximal direction would be in the direction indicated by arrow 54 and displacements in the distal direction would be in the direction indicated by arrow 56. Rotational displacements about proximal/distal axis 54 would be as indicated by arrow 58. FIG. 2 also shows a medial/lateral axis 60 which is perpendicular to proximal/distal axis 54 and oriented to indicate sidewise displacements. Accordingly, medial and lateral displacements would be in directions respectively indicated by arrow 62 and arrow 64. The coordinate system is completed by reference to FIG. 2A where anterior/posterior axis 66 is shown. It is to be understood that anterior/posterior axis 66 is perpendicular to the plane defined by proximal/distal axis 52 and medial/lateral axis 60. Further, it will be understood that the direction for anterior displacements is indicated by arrow 68 and the direction for posterior displacements is indicated by arrow 70.

Within the established coordinate system, it is expected there will be some normal movement and consequent displacement of tibia 36 relative to femur 34. As will be appreciated by the orthopedic surgeon, however, disruptions of knee ligaments from various causes will result in significant variations from what is considered normal. This is particularly so where anterior cruciate ligament 48 is concerned. The extent of these variations is often of great importance for determining the need for or the consequent efficacy of reconstructive surgery. Accordingly, the actual movement of tibia 36 relative to femur 34, in response to an applied force of predetermined magnitude, can be most helpful to the surgeon in deciding upon proper preoperative or postoperative treatment for the patient. Of particular importance in this regard are the specific measurements which include the extent of translational displacement of tibia 36 in an anterior/posterior direction and in a medial/lateral direction. Also important is its rotational displacement about the proximal/distal axis. Arthrometer device 10 is used to make these measurements.

Figure 3:
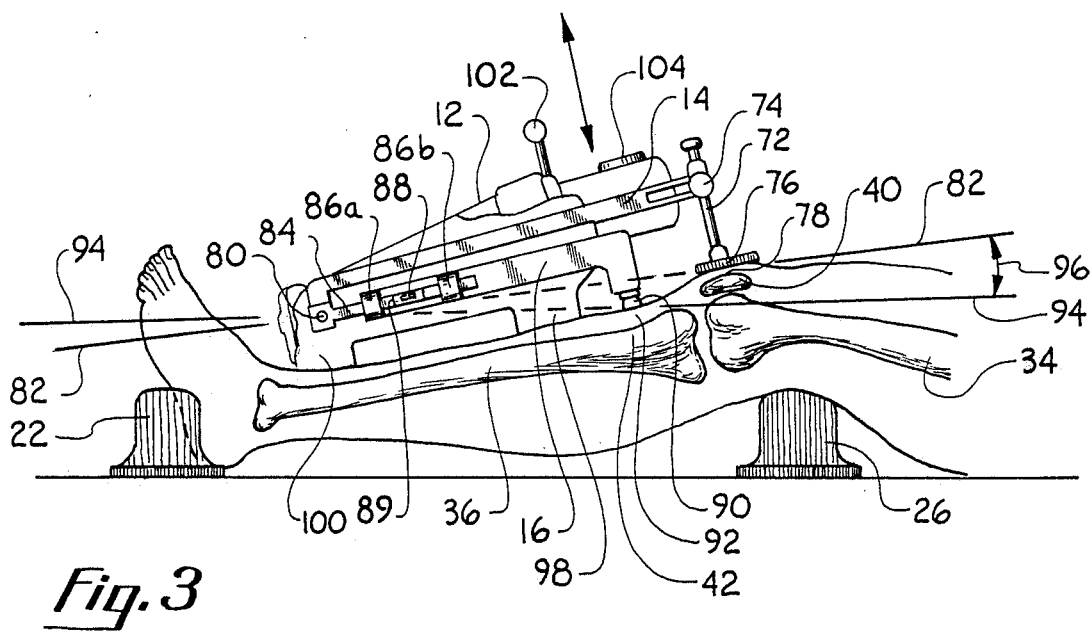
FIG. 3 is a side view of the device with portions cut away for clarity.

Referring now to FIG. 3, it can be seen that patella reference arm 14 comprises an extension rod 72 which is slidingly attached to the proximal end of arm 14 and oriented substantially perpendicular thereto. An adjustment knob 74 is provided to fixedly hold the extension rod 72 onto reference arm 14 during the operation of device 10 for purposes to be subsequently discussed. A sensor pad 76 is attached to extension rod 72, substantially as shown in FIG. 3, for resting at contact point 78 over the patella 40. As intended by the present invention, manipulation of knob 74 allows for adjustment of the relationship between patella reference arm 14 and extension rod 72 to properly position sensor pad 76. As shown in FIG. 3, the distal end of patella reference arm 14 is attached to case 12 at hinge pin 80. With this attachment, patella reference arm 14 can be rotated with respect to case 12 about hinge pin 80. Further, hinge pin 80 and contact point 78 establish the location of reference line 82. As will be more clearly appreciated with subsequent disclosure, the location of reference line 82 provides the basis for measuring displacements between patella 40 and tibial tubercle 42.

FIG. 3 also shows that a member 84 is attached to hinge pin 80. This attachment allows member 84 to rotate with respect to case 12 about hinge pin 80 in a manner similar to that allowed for patella reference arm 14. Further, FIG. 3 shows that brackets 86a and 86b are mounted on tibia reference arm 16 to slidingly receive member 84. A magnet 88 is positioned and held on member 84 for movement therewith. A Hall effect device 89 (shown in phantom) of a type well known in the art, is positioned and held on tibia reference arm 16 generally opposite magnet 88 to generate a signal proportional to the position of magnet 88 relative to the Hall effect device 89.

Still referring to FIG. 3, it can be seen that a paddle 90 is mounted on the proximal end of tibia reference arm 16. Paddle 90 is positioned to rest on a contact point 92 which is next to tibial tubercle 42. With this structure, a measurement line 94 is established between hinge pin 80 and contact point 92. Thus, since reference line 82 and measurement line 94 intersect at hinge pin 80, the angle indicated by arrow 96 between lines 82 and 94 is proportional to the distance between contact point 78 and contact point 92.

Case 12 is formed with a proximal pad 98 and a distal pad 100 which respectively urge against proximal and distal portions of tibia 36 substantially as shown in FIG. 3. A force-application handle 102 is rigidly attached to case 12 to transmit an applied force to the pads 98 and 100. A displacement indicator 104 is affixed to case 12 and electrically connected by circuitry (not shown) which is well known in the pertinent art to display signals that are indicative of specifically identified displacements between tibia 36 and patella 40. These measurements and structure for making them will be more fully appreciated with reference to FIGS. 4 and 5.

Figure 4:
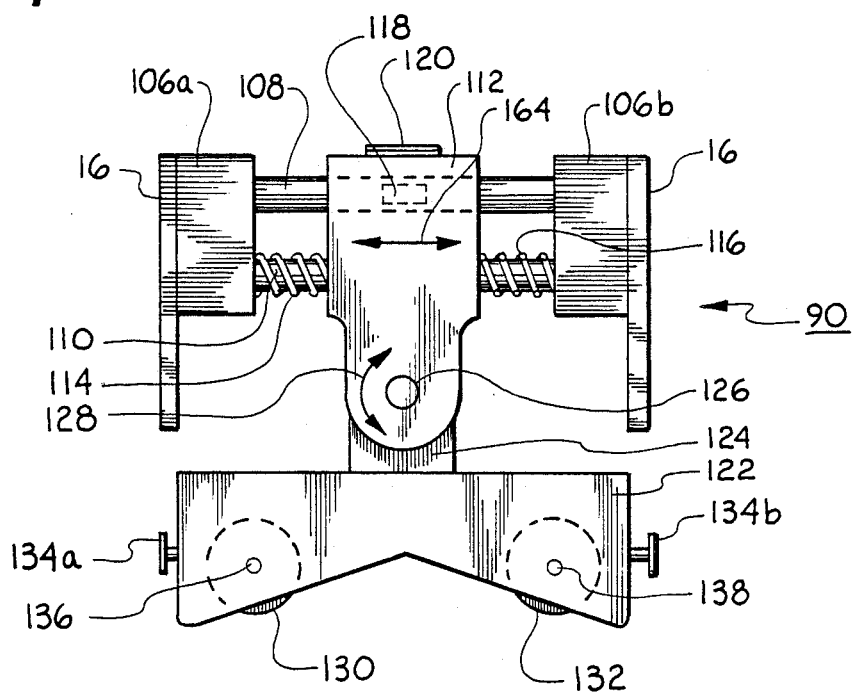
FIG. 4 is a front elevation view of the tibial mount and yoke combination of the device.

In FIG. 4, paddle 90 is seen as it would be viewed from a proximal perspective 54 looking generally along the proximal/distal axis 52 when device 10 is placed on lower leg 18. From this view point, paddle 90 is seen to comprise a pair of mounts 106a and 106b which are attached to tibia reference arm 16 in any manner well known in the art, such as by bolting or gluing. Extending between mounts 106a and 106b, and attached thereto, are a tube 108 and a shaft 110 which are substantially parallel to each other. A mount 112 is slidingly disposed on tube 108 and shaft 110 and yieldingly held thereon in a central position between bases 106a and 106b by the opposed action of spring 114 and spring 116. More specifically, spring 114 is disposed around shaft 110 between base 106a and mount 112. With this structure, mount 112 is moveable between bases 106a and 106b with an equilibrium position substantially central therebetween.

A magnet 118 is positioned and held on tube 108 substantially as shown in FIG. 4. A Hall effect device 120 is fixedly attached to mount 112 for movement with the mount 112 along tube 108 at variable displacements from magnet 118. Electronic circuitry (not shown) is connected with the Hall effect device 120 to receive signals from the device 120 which indicate the relative position, and hence the displacement, of mount 112 with respect to magnet 118.

FIG. 4 also shows that paddle 90 comprises a yoke 122 which is generally U-shaped. A connector 124 is attached to yoke 122 substantially midway between the ends of the "U" and a pivot shaft 126 is attached between connector 124 and mount 112 to permit rotational motion between yoke 122 and mount 112. As shown, this rotation between yoke 122 and mount 112 will be in the directions indicated by arrow 128. Yoke 122 also has a prong 130 and a prong 132 which are positioned on yoke 122 at points substantially equidistant from pivot shaft 126. Prongs 130 and 132 can be either fixed in their attachments to yoke 122 or can be rotatably mounted thereon. As shown in FIG. 4, the prongs 130 and 132 are rollers which are respectively able to rotate about the points 136 and 138. Importantly, if the prongs 130 and 132 are moveable on yoke 122, points 136 and 138 must be fixed relative to pivot shaft 126. Otherwise, the prongs 130 and 132 must themselves be fixed relative to pivot shaft 126. FIG. 4 also shows that yoke 122 includes a pair of strap hangers 134a and 134b which extend from yoke 122 substantially as shown to engage with retainer strap 32 for purposes to be subsequently discussed.

FIG. 5 shows that a magnetic rotor 140 is attached to pivot shaft 126 for rotation therewith. As also shown, a Hall effect device 144 is fixedly held on mount 112 to generate a signal which is indicative of rotational displacements between rotor 140 and device 144. As will be easily appreciated, this relative displacement between rotor 140 and device 144 is also indicative of displacements between yoke 122 and mount 112. Electronic circuitry (not shown) is used to sense the relative movement of various components of the device 10 and generates signals indicative of such movements. Further, various configurations of these electronic elements (not shown), all of which are well known in the pertinent art, can be established for the purposes of the present invention. Also, it will be appreciated that mechanical indicators which measure the relative movement of components of device 10 under operative conditions may also be used. In any event, it is to be understood that several different means well known in the pertinent art can be selectively incorporated into device 10 to make the desired measurements of tibia/patella displacements.

In an alternate embodiment of the paddle 90 as shown in FIG. 6, a brace 146 is attached to tibia reference arm 16. An extension 148 is secured to brace 146 and a magnetic roller 150 is mounted for rotation on the extension 148 in the directions generally indicated by arrow 152. A Hall effect device (not shown) is mounted on extension 148 to generate a signal which is indicative of the relative position between roller 150 and extension 148. Accordingly, rotational displacements of roller 150 with respect to extension 148 can be measured.

The alternate embodiment of paddle 90 requires cooperative engagement with a leg adapter 156 which needs to be attached to lower leg 18 in the general area of tibial tubercle 42. As shown in FIG. 6, leg adapter 156 comprises a relatively hard arcuate surface 158 which rests on a bed 160 which is conformable to the contour of the lower leg 18. As will be appreciated by the skilled artisan, bed 160 can incorporate any conformable substance and thus could include such diverse materials as vacuum packed plastic granules or compressed air. A strap 162 is used to hold adapter 156 against lower leg 18 and present arcuate surface 158 for engagement with roller 150. Importantly, arcuate surface 158 is hard and is uniformly rounded so that roller 150 can freely and predictably roll over the surface 158.

OPERATION

In the operation of the preferred embodiment of device 10, case 12 is positioned on lower leg 18 with distal pad 100 located at the distal end of tibia 36. At this location, and with the lower leg generally positioned between foot support 22 and thigh support 26, it can be assumed that hinge pin 80 will remain effectively stationary during the operation of device 10. With case 12 so positioned, distal strap 28 and proximal strap 30 are engaged to hold case 12 against lower leg 18. Sensor pad 76 is then positioned over contact point 78 next to patella 40. With the assumptions that cutaneous movement near patella 40 is negligible and that patella 40 maintains a substantially fixed relationship with respect to femur 34, contact point 78 and reference line 82 can be used as a basis from which displacements of tibial tubercle 42 can be measured.

Once case 12 is in place, paddle 90 will be positioned with prongs 130 and 132 resting on the flares of tubercle 42. Specifically, in the case where lower leg 18 is of the left leg, prong 130 will rest against lateral flare 44 and prong 132 will rest against medial flare 46. Retainer strap 32 is then engaged with strap hangers 134a and 134b and adjusted to hold prongs 130 and 132 of yoke 122 against the respective flares 44 and 46. Device 10 is now positioned to measure knee stability as predominantly provided by cruciate ligaments 48 and 50 and other ligaments and tendons of the knee. While the orthopedic principles and purposes obtained from these measurements are beyond the required scope of this disclosure, a thorough understanding of these principles and purposes is set forth in the following series of articles which are incorporated herewith by reference. "Instrumented Measurement of Anterior Laxity of the Knee," by Dale Daniel et al., "The Journal of Bone and Joint Surgery," Volume 67-A, No. 5, pp. 720–726, June 1985. "Instrumented Measurement of Anterior Knee Laxity in Patients with Acute Anterior Cruciate Ligament Disruption," by Dale Daniel et al., "The American Journal of Sports Medicine," Volume 13, No. 6. "The Measurement of Anterior Knee Laxity After ACL Reconstructive Surgery," by Lawrence Malcom et al., "Clinical Orthopaedics," June 1985.

The actual testing of knee stability is accomplished by applying a force of predetermined magnitude to force-application handle 102. This force is transmitted through case 12 to proximal pad 98. Depending on the integrity and strength of the ligaments connecting femur 34 to tibia 36, tubercle 42 will be displaced from patella 40 in response to this applied force. A posterior force on lower leg 18 (i.e. in the direction of arrow 70) will be directly applied by case 12 through proximal pad 98. An anterior force on lower leg 18 (i.e. in the direction of arrow 68) will be applied by proximal strap 30. In response to either an anterior or a posterior force, several movements of structure within device 10 result which can be used to measure displacements of tibia 36 from femur 34. Specifically, these measurements pertain to displacements of tibia 36 from femur 34 to include: anterior/posterior translational displacements (i.e. in the direction of arrows 68 and 70); medial/lateral translational displacements (i.e. in the directions of arrows 62 and 64); and rotational displacements about the proximal/distal axis 52 (i.e. in the direction of arrow 58).

In accordance with the present invention, anterior/posterior translation displacements will be proportional to changes in the angle 96 between reference line 82 and measurement line 94 as indicated by magnet 88 and its associated Hall effect device 89. Further, medial/lateral translational displacements will be proportional to the movement 112 in the directions of arrow 164 as indicated by magnet 118 and its associated Hall effect device 120. Still further, rotational displacements about proximal/distal axis 52 will be proportional to the movement of rotor 140 relative to its associated Hall effect device 144.

With the alternate embodiment of paddle 90, the anterior/posterior translational displacement of tibia 36 from femur 34 will be measured in the same manner as disclosed above for the preferred embodiment. The medial/lateral translational displacements of tibia 36 relative to femur 34, however, are combined into a single measurement taken from the rotation of roller 150 as indicated by its movement relative to a Hall effect device (not shown).

It is to be understood that while measurements of the various displacements discussed above have been taken from indications that result from relative movement between a magnet and a Hall effect device, any well known linear or angular measuring device will suffice for purposes of the present invention. Importantly with the obtained measurements, the orthopedic surgeon is able to obtain sufficient information to diagnose the degree of knee stability and prescribe effective corrective measures as required.

While the particular knee ligament testing device as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

We claim:

1. A device for measuring displacement of the tibia with respect to the patella in response to an applied force on the tibia which comprises:
   an elongated first reference arm having a distal end and a proximal end;
   a second reference arm having a distal end pivotally engaged to said distal end of said first reference arm, a proximal end, and means attached to said proximal end for stationarily resting said proximal end on the patella;
   a shaft fixedly attached to said proximal end of said first reference arm and oriented substantially perpendicular to the longitudinal axis of said first reference arm;
   a mount slidingly engaged with said shaft;
   a paddle attached to said mount, said paddle comprising means for resting said paddle on the tibia;
   means for generating a first signal proportional to the angled relationship between said first reference arm and said second reference arm; and
   means for generating a second signal indicative of the position of said mount relative to said first reference arm.

2. A device for measuring displacements of the tibia with respect to the patella as recited in claim 1 wherein said paddle further comprises:
   a yoke pivotally attached to said mount for rotation relative to said mount about an axis substantially parallel to said first reference arm; and
   means for generating a third signal indicative of the position of said yoke relative to said mount.

3. A device for measuring displacements of the tibia with respect to the patella as recited in claim 2 wherein said resting means comprises said yoke, said yoke having a first prong and a second prong, said first prong and said second prong being respectively positionable on the lateral flare and the medial flare of the tibia to rest said paddle on the tibia.

4. A device for measuring displacements of the tibia with respect to the patella as recited in claim 3 further comprising means for securing said device to the tibia and means for holding said proximal end of said second reference arm against the patella.

5. A device for measuring displacements of the tibia with respect to the patella as recited in claim 4 further comprising means for applying a predetermined force to the tibia in the general anterior/posterior direction.

6. A device for measuring relative displacements of the tibia from the patella which comprises:
   a reference member having a first end, said first end having first means for resting said first end on the patella and having a second end, said second end having second means for resting said second end distally on the tibia;
   a measurement member having a first end, said first end of said measurement member having means for resting said first end of said measurement member on the proximal end of the tibia, said measurement member having a second end pivotally attached to said second end of said reference member, said second end of said measurement member being rotationally movable relative to said reference member between a first portion wherein said tibia is effectively unforced and a second position wherein said tibia is subject to a predetermined anterior/posterior force;
   a paddle slidingly attached to said first end of said measurement member, said paddle being movable in a direction substantially perpendicular to said measurement member;
   means to generate a first signal proportional to the angle between said reference member and said measurement member as said measurement member is moved from said first position to said second position; and
   means to generate a second signal proportional to the displacement of said paddle as said measurement member is moved from said first position to said second position.

7. A device as recited in claim 6 wherein said paddle comprises:

a shaft fixedly attached to said proximal end of said measurement member and oriented substantially perpendicular to the longitudinal axis of said measurement member;

a mount slidingly engaged with said shaft; and a yoke pivotally attached to said mount, said yoke being rotationally movable about the longitudinal axis of said measurement member, said yoke having a first prong and a second prong said first prong and said second prong being respectively positionable on the lateral flare and the medial flare of the tibia to rest said paddle on the tibia.

8. A device as recited in claim 7 further comprising means for generating a third signal indicative of the rotation of said yoke relative to said mount as said measurement member is moved from said first position to said second position.

9. A device as recited in claim 8 further comprising means for securing said device to the tibia and means for holding said proximal end of said reference member against the patella.

10. A device as recited in claim 9 further comprising means for applying a predetermined force to the tibia in the general anterior/posterior direction.

11. A device for measuring displacement of the tibia with respect to the patella in response to an applied force on the tibia which comprises:

a reference arm having a pad attached thereto for resting on the patella;

a measurement arm pivotally attached to said reference arm to establish a fulcrum therebetween;

a roller pivotally mounted on said measurement arm, for rotation about an axis substantially parallel to the longitudinal axis of said measurement member, said roller being adapted to rest against said tibia;

means for measuring angular displacements at said fulcrum between said reference arm and said measurement arm to indicate the anterior/posterior displacement of the tibia from the patella; and means for measuring the rotation of said roller to indicate medial/lateral displacement of the tibia from the patella.

12. A device for measuring displacement of the tibia with respect to the patella as recited in claim 11 further comprising a cuff attached to said device, said cuff being surroundingly positionable on the tibia, said cuff having an arcuate surface operatively engageable with said roller.

13. A device for measuring displacement of the tibia with respect to the patella as recited in claim 12 further comprising means for applying a predetermined force to the tibia in the general anterior/posterior direction.

14. A device for measuring displacement of the tibia with respect to the patella as recited in claim 13 further comprising means for securing said device to the tibia and means for holding said proximal end of said reference arm against the patella.

15. A device for measuring displacement of the tibia with respect to the patella as recited in claim 14 wherein said arcuate surface is shaped as a semi-circle.

16. A device for measuring displacement of the tibia with respect to the patella as recited in claim 15 wherein said cuff comprises a cavity filled with a pliable material for conforming said cuff to the tibia.

* * * * *